United States Patent [19]

Nash

[11] 4,330,282

[45] May 18, 1982

[54] ROTOR DRIVEN VIBRATORY DEVICE HAVING ROTOR CENTRALIZATION MEANS AND VIBRATIONAL MODE SELECTION MEANS ASSOCIATED THEREWITH

[75] Inventor: John E. Nash, Downington, Pa.

[73] Assignee: Syntex (U.S.A.) Inc., Palo Alto, Calif.

[21] Appl. No.: 91,016

[22] Filed: Nov. 5, 1979

[51] Int. Cl.³ .......................... A61C 1/07; A61C 3/03
[52] U.S. Cl. .................................................. 433/118
[58] Field of Search ............... 433/120, 118, 119, 122, 433/123, 124, 143, 172; 54/59 SS; 173/57, 79; 415/503

[56] References Cited

U.S. PATENT DOCUMENTS 2,960,314 11/1960 Bodine, Jr. ......................... 51/59 SS
3,811,190 5/1974 Sertich .................................. 433/118

Primary Examiner—Robert Peshock
Attorney, Agent, or Firm—John A. Dhuey; Joseph I. Hirsch

[57] ABSTRACT

A dental scaler is disclosed wherein an air-driven rotor is driven about a shaft to impart vibrations thereto and drive a work tool or other object attached to the shaft. The vibratory device includes means on the shaft for correcting displacement of the rotor from its drive position. That means comprises a portion of the shaft beneath the rotor means having an enlarged diameter such that movement of the rotor caused by shaft wear is corrected. Additional means may be associated with the rotor, e.g., chamfered end edges of the rotor, which minimize pressure differentials at the end of the rotor edges and consequently assist in centralization of the rotor about the outlet means on the shaft. The fluid outlet means comprises outlet ports in the shaft wall beneath the area of rotation of the rotor, the outlet ports having chamfered outside end edges to minimize power losses from turbulence. Additionally, means are provided along the shaft for selecting the vibrational mode in which the vibratory device operates.

72 Claims, 5 Drawing Figures

U.S. Patent   May 18, 1982   Sheet 1 of 2   4,330,282
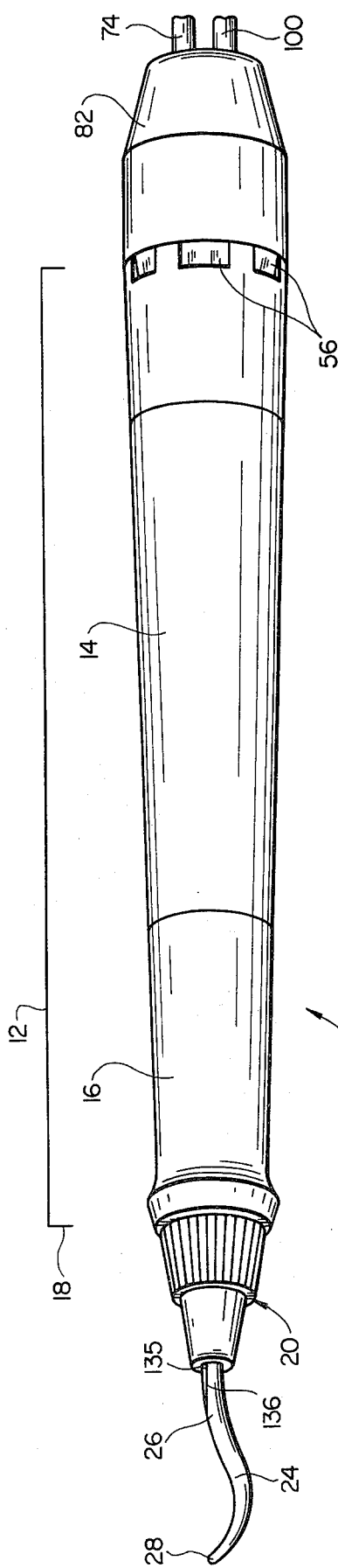
FIG_1
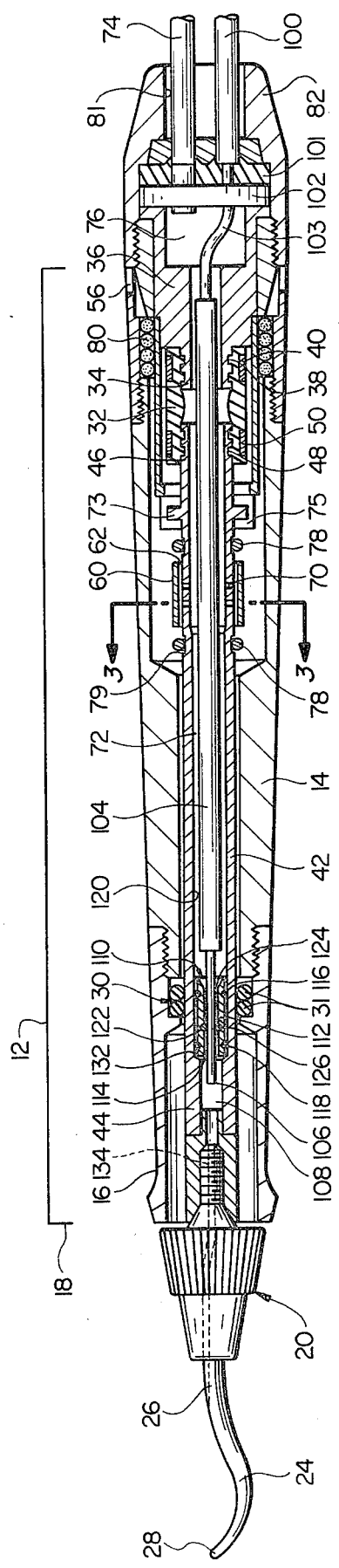
FIG_2

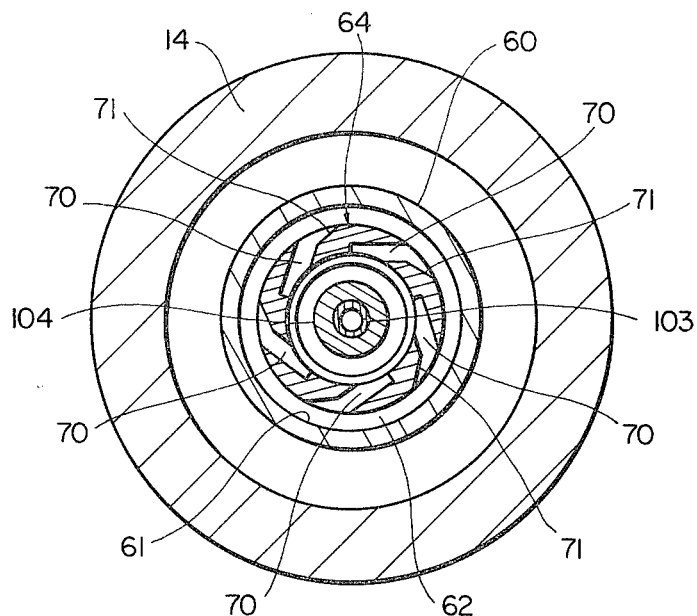
FIG_3
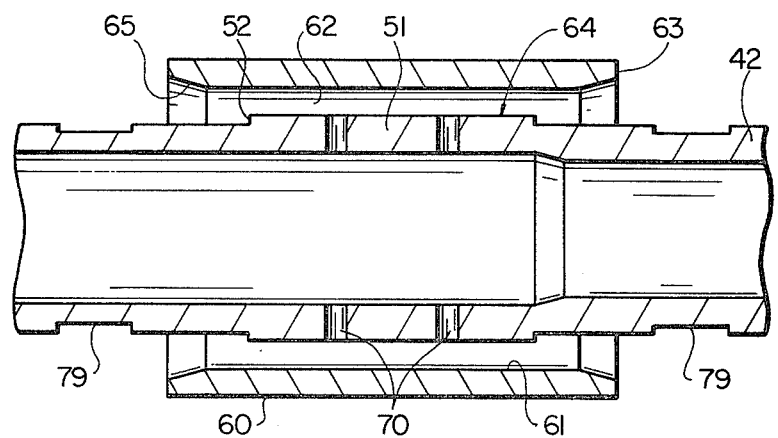
FIG_4
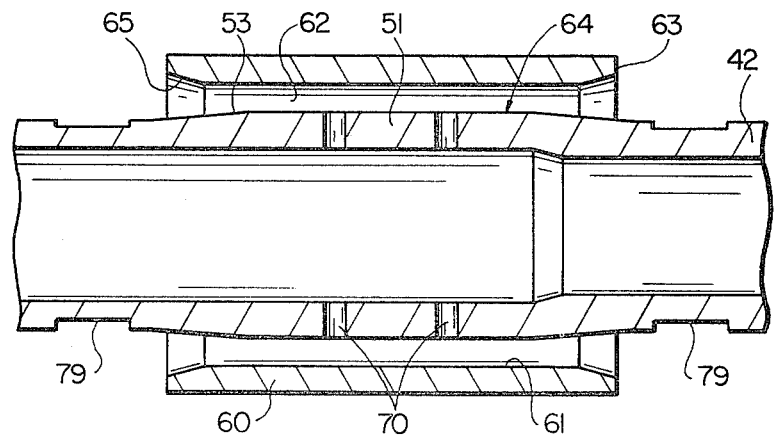
FIG_5

ROTOR DRIVEN VIBRATORY DEVICE HAVING ROTOR CENTRALIZATION MEANS AND VIBRATIONAL MODE SELECTION MEANS ASSOCIATED THEREWITH

BACKGROUND OF THE INVENTION

1. Field

Power driven dental scalers are well known. Of particular interest herein are those dental scalers driven by means of a fluid exiting through outlet ports in a shaft and impinging upon a rotor disposed on the shaft to impart vibrational movement to the shaft.

2. State of the Art

Of the power driven dental scalers currently available, most common are scalers utilizing a flow of compressed air or an electrical ultronsonic transducer to cause a scraping-type work tool to vibrate.

Typical of the earlier air-driven dental scalers are those of U.S. Pat. Nos. 3,820,529 and 3,444,622 to Miles et al, which scalers utilize an air-driven ball contained in a chamber. Movement of the ball against the walls of the chamber imparts vibration to the chamber which vibrations are then transmitted to the scraping tool.

A more recent type of air-driven scaler, described in U.S. Pat. No. 3,526,962 to Fuerst, utilizes a rotatable mandrel which has an irregularly-shaped tip engaged with a reciprocal block in which the mandrel tip is received.

It is characteristically a problem of these air driven scaler that much of the vibrational energy generated by the vibrator motor is transferred to the handle portion of the dental scaler rather than to the scraper tool. Moreover, the modes of vibration of these scalers may change as moving parts of the vibration generating mechanism wear with time.

In U.S. Pat. No. 3,703,037 to Robinson, there is described a dental scaler which utilizes an electrical ultrasonic transducer to provide constant modes of vibration for coupling with particular types of work tools. One disadvantage of the ultrasonic scaler, however, is the cost of the transducer and its associated ultrasonic generator.

A recent improvement in air-driven dental scalers is disclosed in U.S. Pat. No. Re. 29,687 to Sertich. This dental scaler has very few moving parts as compared to the aforementioned mechanically complicated air-driven scalers and provides efficient transfer of vibrational energy to a scraping-type work tool with relatively little vibration being transferred to the handle portion of the instrument. The Sertich-type scaler provides uniform modes of constant vibration which may be matched with the vibratory modes of various types of work tools without the need for any complicated electronic components.

The Sertich-type scaler utilizes a rotor disposed on a shaft which is driven by a fluid media such as air to propel the rotor rotatably about the shaft and impart vibratory motion thereto. The rotor and the outside surface of the shaft provide a gap into which air flow occurs through outlet ports dispoded in the wall of the shaft beneath the rotor. The air impinges on the inner surface of the rotor causing it to rotate about the shaft in a manner which creates a vibrational movement in the shaft which is transmitted to a work tool connected to the shaft. In order to operate properly, it is necessary that the rotor remain disposed over the air outlet ports on the shaft, and in order to obtain maximum efficiency, it is necessary to have the rotor rotate freely about the shaft at a position centralized axially over the air outlet ports. Rotation of the rotor about the shaft tends to create wear on the outside surface of the shaft. That wear can induce a pattern of unequal fluid flow out of the space defined by the ends of the rotor and the shaft. The corresponding pressure differentials set up at the ends of the rotor can cause the rotor to be displaced from its position over the outlet ports, which greatly decreases the efficiency of operation of the device. Accordingly, there is a need for a means for compensating for wear induced by the rotor on the shaft surface and for continuously correcting axial displacement of the rotor from a centralized position above the outlet ports on the shaft.

An aspect of mechanical vibratory devices is that they tend to operate at certain well-defined frequencies. Those frequencies are influenced by the particular mass distribution along the shaft of the device and the location of the support means for the shaft. It has heretofore been unappreciated that not only is the location of the support means on the shaft important for determining the resultant vibrational frequencies at which the device operates, but that the particular resilient characteristics of the support means can be critical in determining and defining an operating frequency which maximizes scaling efficiency, without creating a need for a substantial increase in power input to move from one mode of resonance to the next. Accordingly, there has been a need for a vibrating device which utilizes particular support means for optimizing the power output of the vibrating device.

SUMMARY OF THE INVENTION

An air driven vibratory-type dental scaler is provided which comprises elongated casing means having a proximal or rearward end and a distal or forward end, support means within the casing means, a substantially rigid hollow shaft supported within the elongated casing means by the support means, work tool connecting means attached to the distal end of the shaft, the work tool connecting means capable of operatively connecting a work tool to the distal end of the hollow shaft, the hollow shaft having fluid media inlet means and outlet means, respectively, for receiving and discharging fluid media, rotor means disposed about the hollow shaft, over the outlet means and being driveable about the hollow shaft by the fluid media, the hollow shaft and the rotor means each having a configuration and disposed with respect to each other so as to define a space therebetween for receiving fluid media from the outlet means during movement of the rotor about the shaft, the flow of the fluid media through the outlet means into the space driving the rotor means rotatively about the shaft to impart vibratory movement to the shaft, the hollow shaft having means thereon for continuously correcting for axial displacement of the rotor means from a position of centralization over the outlet means when the rotor is being driven about the shaft. Additional correction means on the rotor means can be provided to further maintain the rotor in a centralized position over the outlet means. The outlet means has means thereon for improving the efficiency of the vibratory device.

In another aspect of the invention, the support means includes first support means near the distal end of the shaft at a node of the standing wave form developed in the shaft in a selected vibratory mode. The first support means is sufficiently non-resilient so as to bias the scaler to operate in the selected vibratory mode and sufficiently resilient to substantially prevent transfer of vibration from the shaft to the scaler casing. The dental scaler can also have water transport means associated therewith for transporting water from an external source to a point near the scaler tip to provide water to the surface of the tooth on which dental work is being conducted. A water seal assembly used in conjunction with the water transport means is supported on the distal end of the shaft at a location substantially the same as the location of the first support means. The location of the first support means is at a node of the shaft at the preferred resonant frequency, thus preventing substantial transfer of vibration from the shaft to the inlet water seal.

The various aspects of the present invention can be used either along or in combination.

DESCRIPTION OF SPECIFIC EMBODIMENTS

The means providing the features and advantages of the present invention are illustrated in the accompanying drawings wherein:

FIG. 1 is a perspective view of a dental scaling instrument of this invention;

FIG. 2 is a longitudinal side elevational view, partly in section, of the dental scaler of FIG. 1;

FIG. 3 is a cross-sectional view of the driving mechanism of the dental scaler of FIG. 2 taken along line 3—3;

FIG. 4 is an enlarged sectional view of the driving mechanism of the dental scaler of FIG. 2; and FIG. 5 is an enlarged sectional view of another aspect of the driving mechanism of this invention.

Illustrated in the drawings in a dental scaling instrument 10 comprising a handle 12 which includes a barrel 14 and a neck 16. Attached to the distal end 18 of scaler 10 is a nose piece 20. Secured within nose piece 20 is a shank 26 of a work tool or tip 24 having a curved end 28. As shown in detail in the cross-sectional view of FIG. 2, handle 12 provides an elongated casing within which is mounted support means comprising a first or front support 30 including a pair of O-rings 31. A second or rear resilient support is provided by a cylindrical tube 32 of resilient material which is sleevably engaged about a boss portion 34 secured to a rigid rear support 36. Boss portion 34 has a retaining grooves 38 circumferentially disposed thereon for retaining resilient rear support 32 by means of retaining ring 40. Disposed substantially coaxially with respect to elongated handle 12 is a vibratable, substantially rigid, hollow shaft 42. Nose piece 20 is threadedly connected to the distal end 46 of hollow shaft 42 and the proximal end of shaft 42 is formed with retaining grooves 48 for engaging resilient rear support 32 therein. A pin 73 is provided on shaft 42 for engaging a wall 75 of a slot in rear support 26 to oppose twisting forces applied to shaft 42 during engagement or disengagement of nose piece 20 with or from the distal end of shaft 42. Rear support 32 is retained within retaining grooves 48 on shaft 42 by means of a retaining ring 50.

As seen most clearly in FIG. 4, shaft 42 is formed with an intermediate section 51 having a diameter greater than the diameter of thos portions of shaft 42 adjacent section 51. Outlet ports 70 are formed in the wall of shaft 42 in the intermediate section 51 and serve to provide fluid communication for fluid media means from the inside of tubular shaft 42 to the space adjacent side wall 64 of shaft 42. Centrally and axially disposed above intermediate portion 51 of shaft 42 is rotor means 60, which defines a gap 62 between its inner surface 61 and side wall 64 of shaft 42 into which fluid media is directed from outlet ports 70.

With reference to FIGS. 1 and 2, a fluid medium, such as compressed air, is supplied from a source (not shown) through a supply tube 74 which passes through an axially disposed opening 81 in end cap 82. The flow of compressed air passes into plenum 76 in through passageway 72 and shaft 42 to fluid media outlet ports 70. The flow of compressed air which exhausts through outlet ports 70 strikes the inner wall 61 of rotor 60 and urges rotor 60 to rotate about shaft 42. Each of the outlet ports 70 has an axis which is offset or spaced at a distance from the longitudinal axis of shaft 42. In that configuration no port axis intersects the longitudinal axis of shaft 42 and each of ports 70 directs a jet of air at a glancing angle with respect to the inner wall 61 of rotor 60 so as to impart rotational movement to rotor 60. The air passes through the end sections of gap 62 into the main barrel section and subsequently passes through muffler means 80 which are supported on rigid rear support 36 to exhaust through outlet ports 56 into the atmosphere.

Stop means 78 are disposed in indented sections or grooves 79 in outer surface 64 of shaft 42. Typically, stop means 78 comprise O-rings sleevably engaged about shaft 42. Stop means 78 prevent excessive travel of rotor 60 so that rotor 60 is at least partially disposed about outlet means 70 at all times, including the time prior to activation of the instrument with compressed air. Thus, when air is supplied to the instrument, the air flowing through outlet ports 70 will contact at least a portion of rotor 60 and initiate its rotational movement about shaft 42. Correction means to be discussed hereinafter are independent of stop means 78 and in normal operation rotor 60 will not contact stop means 78. A description of the manner in which the spinning rotor 60 imparts vibrational movement to shaft 42 may be found in the aforementioned U.S. Pat. No. Re. 29,687, the disclosure of which is incorporated herein by reference.

The dental scaler can include means for transporting water from an external source to a work tool 26 at its curved end 28. A first water transport hose 100 located at the rearward or proximal end of scaler 10 is mounted in a detachable coupling 101. First water hose 100 is connected to an external source of water (not shown), the forward end of the hose being connected to one end of a rigid tube 103 which passes through a passageway in support body 102. Tube 103 is disposed substantially coaxially with respect to hollow shaft 42. Water transport tube 103 extends through hollow shaft 42 toward the distal end of scaler 10 and terminates distally from water seal assembly 110. Tube 103 is covered with an elastomeric tube covering 104 to dampen vibration build-up within tube 103. The forward or distal end 106 of water tube 103 extends into plenum 108.

Water tube end 106 is supportably received within a water seal assembly 110 located at the forward or distal end of dental scaler 10. Water seal assembly 110 comprises a cylindrical body 112 having a passageway 114 coaxially disposed with respect to the axis of body 112. Running circumferentially about the outer side wall of cylindrical body 112 are a pair of spaced annular grooves 116, one adjacent each end cylindrical body 112. Disposed within each of grooves 116 is an O-ring 118 fabricated of a resilient material. O-rings 118 serve to position cylindrical body 112 within the forward end of hollow shaft 42 by frictional engagement of O-rings 118 with portions of inner wall 120 of shaft 42. Within a midportion of cylindrical body 112 is a chamber formed by an annular groove 122 running circumferentially along a portion of inner wall 124 of body 112 between grooves 116. Contained within groove 122 is an O-ring 126 which is in frictional engagement with the walls of groove 122 and with a portion of water tube 106. O-ring 126 helps to properly position tube 104 centrally within hollow shaft 42. Positioning of the center of gravity of water seal assembly 110 slightly forwardly of first support 30, i.e., toward the distal end of scaler 10, imparts a force on cylindrical body 112 tending to move it in a forward axial direction toward the distal end of scaler 10, thereby ensuring continuous contact between cylindrical body 112 and shoulder 132 of shaft 42. A more detailed description of the manner in which sealing between the water assembly 110 and shaft 42 is effected is provided in my copending application Ser. No. 26,378, filed Apr. 2, 1979, the disclosure of which is incorporated herein by reference.

A second water transport tube 134 extends between the distal and proximal ends of nose piece 20 within a central bore formed therein. End 135 of tube 134 is positioned within a groove 136 on shank 26 of tool 24. Water from plenum 108 flows through nose piece 20 within tube 134 to end 135 and groove 136 and over the surface of tool 24 to the vicinity of tip 28 where it is atomized by the vibratory action of tip 28.

In one aspect the present invention comprises first means on shaft 42 for continuously correcting axial displacement of rotor 60 from a centralized location above outlet ports 70. As illustrated with particularity in FIG. 4, the correction means comprises section 51 of shaft 42 having a diameter greater than the diameter of those portions of shaft 42 adjacent section 51 and being generally of a length less than the length of rotor 60. Section 51 is thus completely disposed within the area of projection of rotor 60 onto shaft 42. Section 51, having a diameter greater than the diameter of shaft 42 adjacent section 51, is formed by a step 52 as shown in FIG. 4. Optionally section 51 can be formed by a ramp or inclined surface 53 as shown in FIG. 5. When an inclined surface 53 is utilized, the ends of the surface joining shaft 42 terminate outwardly of the area of projection of rotor 60 onto shaft 42.

In normal operation the flow of air exiting through gap 62 from each end of rotor 60 creates balanced drag forces in both the distal and proximal axial directions. However, when rotor 60 is displaced from an axially centralized position above outlet ports 70, the axial drag forces tend to become unbalanced. Also, when the fluid flowing from ports 70 exits from the ends of gap 62 between rotor 60 and outer wall 64 of shaft 42, eddies are set up near the ends of rotor 60, which tend to suck air in over the edges of rotor 60 and create low pressure regions. When rotor 60 is centralized above outlet ports 70 the pressure losses associated with the eddies are balanced and the rotor tends to remain in a centralized position. In actual practice since shaft 42 may not be perfectly cylindrical, and because rotor 60 does not rotate in a perfect cylindrical fashion about shaft 42, the conical whirl set up by rotor 60 has an axial force component which also tends to shift the position of rotor 60. When the sum of the conical whirl axial force and the eddy force exceed the differential drag force on rotor 60, rotor 60 will tend to move in an axial direction displacing it from the centralized position over outlet ports 70. Non-parallel rotation of rotor 60 about shaft 42 tends to create wear on outer surface 64 of shaft 42 thus changing the size of gap 62 during operation of the vibratory device. In the absence of enlarged diameter section 51 on shaft 42, such wear creates substantial deviations in the size of gap 62 and upsets the force balance which tends to hold rotor 60 in a centralized position over outlet ports 70.

Step 52 or ramp 53 at each end of section 51 of shaft 42 creates an enlarged gap between outer surface 64 of shaft 42 and rotor 60 which compensates for small upsets in the placement of rotor 60. Accordingly, movement of rotor 60 in an axial direction raises the eddy pressure in the area at end of rotor 60 which is in the direction of axial movement and lowers the eddy pressure in the area at the end of rotor 60 which is away from the direction of axial movement of rotor 60. The instantaneous differential eddy pressure then existing tends to move rotor 60 back into a position centralized over outlet ports 70 so that the sum of the forces on rotor 60 remains balanced. In that manner wear on outer surface 64 of shaft 42 which tends to create an imbalance of forces on rotor 60 is compensated for and rotor 60 remains essentially centralized over outlet ports 70.

As is apparent from the preceding discussion, it is desired to balance the pressure forces at each end of rotor 60 such that the balance of forces tends to keep rotor 60 in a centralized position over outlet ports 70. In another aspect of the invention, rotor 60 is provided with chamfers 65 at end edges 63 which assist in balancing the eddy forces at each end of rotor 60. For more exact control of the eddy forces, it is desired to have inner surfaces 61 of rotor 60 from any radially extending burrs particularly at chamfered end portions 65. Typically, chamfers 65 are between about 30°–65° as measured from the longitudinal axis of rotor 60, with a chamfer of about 40°–50° being presently preferred. Because of the stresses induced in rotor 60 upon rotation about shaft 42, it has been found that control of the surface roughness of inner surface 61 of rotor 60 is important to increase the lifetime of operation of the instrument without failure of rotor 60. Thus, in another aspect of the invention the surface roughness of inner surface 61 of rotor 60 is maintained smoother than about 20 micro-inches.

Enlarged cylindrical section 51 of shaft 42 is typically about 0.001–0.002 inch greater in its diametral dimension than the lesser diameter portions of shaft 42 adjacent section 51. Section 51 is of a length less than the length of rotor 60, such that the area of projection of rotor 60 onto shaft 42 completely encompasses section 51. Typically, the ratio of the length of cylindrical section 51 to the length of rotor 60 is between about 0.85–0.97.

First correction means comprising enlarged section 51 can be used alone, but it is desirable to use enlarged section 51 in conjunction with chamfered end edges 65 of rotor 60 to provide a second correction means associated with rotor 60.

In a further aspect of this invention, outlet ports 70 can be provided with chamfers 71 on the outside end edges thereof, as shown in FIG. 3, in order to increase the efficiency of the vibratory device of this invention. Chamfers 71 on the end edges of outlet ports 70 minimize eddy formation and consequently reduce pressure losses due to turbulence created by formation of eddies at the ends of outlet ports 70. Chamfers 71 can be about 15°–45° as measured from the central axis of each outlet port 70 and typically are about 30°. The axis of each of outlet ports 70 is spaced from the longitudinal axis of shaft 42.

It is characteristic of a vibratory device of the type herein described that it tends to operate in a vibrational mode corresponding to a resonance frequency of the device. In practice, there are practical limitations on the amount of power which can be put into the device so as not to bring about mechanical failure of the components of the device due to stresses imposed thereon. Accordingly, it is not always possible or desirable to shift from one resonance frequency to the next by increasing power input into the device. However, it remains desirable to operate the device in certain vibrational modes to obtain operating characteristics which enhance the operative function which the device is intended to produce.

For example, in the field of dental scalers, it is desireable to operate at high frequencies and low vibrational amplitudes of the scaler tip to increase scaling efficiency and enhance patient comfort. In order to bias the device to operate in a selected vibrational mode which has desirable operating characteristics, the first support means 30 should be formed of a material which is relatively non-resilient, e.g. less than 70% resilient, and located at a node of the standing wave form developed in scaler 10 in the selected vibrational mode. In that manner, unwanted vibrational modes, i.e. those having resulting frequencies which tend to limit scaling efficiency and decrease patient comfort, are eliminated.

In its present embodiment, scaler 10 tends to operate in one vibrational mode having a frequency of about 4000 cycles per second and in another vibrational mode having a frequency of about 6000 cycles per second. When scaler 10 operates in the 4000 cycles per second mode, scaling efficiency is reduced and patient comfort is decreased relative to the 6000 cycle per second mode, due in part to the larger amplitudes of vibration present at tip 28 in the 4000 cycles per second mode.

When a material having a high resiliency, i.e. greater than 70% resilient, is utilized in first support means 30, scaler 10 tends to operate in the undesired, lower frequency mode. It will not automatically, and without a substantial increase in power input, shift into the desired, higher frequency mode. However, when first support means 30 is formed of a material less than 70% resilient, e.g. about 60% resilient, and is located at a node of the standing wave form developed in shaft 42 in the desired, high frequency, vibrational mode, the bias induced by that structure insures that the operating mode of scaler 10 will be at the selected or desired, higher frequency mode. While first support 30 is formed of a sufficiently non-resilient material so as to bias scaler 10 to a selected vibrational mode, if does have a resiliency sufficient to dampen vibrations which might be transferred from shaft 42 to handle 12. Because first support 30 is located at a node of the standing wave form developed in shaft 42 in the selected operating mode, the amplitude of vibrations of shaft 42 at the location of first support 30 will be small and little or no power will be absorbed by the support. The finite dimension of the support requires that a certain amount of material be disposed on either side of the theoretical node, and, accordingly, small amplitudes of vibration will exist at the location of first support 30.

The location of first support 30 for a selected vibrational mode can be determined by bench operation of the scaler with the casing removed. Drive air is supplied to the unit and shaft 42 can be clamped with a suitable damping means at various locations along its length. Pinching of shaft 42 between the fingers of a hand is one suitable method although other methods could be used. Damping of shaft 42 at various locations along its length causes shaft 42 to operate in particular vibrational modes depending on the location of the damping force. From those generated modes, an operting mode is selected and first support 30 is located at the position at which the damping force created the selected operational mode.

It will be appreciated that the particular vibrational mode selected will depend to some extent on the nature of the function to be performed by the vibratory device. For example, whereas one vibrational mode may be selected for dental applications, i.e. one having low vibrational amplitudes at the tip to enhance patient comfort, another vibrational mode might be selected for an operation such as scale removal from or deburring of a metal surface wherein comfort to a patient is not a consideration. In the latter applications, large vibrational amplitudes at the tip may be desirable.

Accordingly, in yet another aspect of the invention, first support means 30 is positioned on shaft 42 at a node of the standing wave form developed in shaft 42 in a selected vibratory mode of scaler 10, and first support means 30 is sufficiently non-resilient so as to bias scaler 10 to operate in the selected vibratory mode. First support means 30 is sufficiently resilient to substantially prevent transfer of vibration from shaft 42 to the casing means of scaler 10. First support means 30 is generally formed of a material less than 70% resilient, e.g. 60% resilient, and can comprise 0-rings 31 of the specified resiliency.

Suitable materials for the support means include compounded nitrile and neoprene synthetic rubbers having desired resiliency nd operating characteristics. Such materials may include, for example, neoprene elastomer, fluorocarbon elastomer, ethylene propylene elastomer, and butadiene/acrylonitrile elastomer. The more resilient materials can be utilized for the rear support and the less resilient for the first or front support. It will be understood that resiliency refers to the ability of the material to recover after deformation and not dissipate energy in its internal structure. For example, a ball of theoretical material being 100% resilient would rebound to about the same height from which it originally was dropped. A ball being 70% resilient would rebound to a height of about 70% of the height from which it originally was dropped, dissipating a certain amount of energy internally.

Utilization of first support means 30 as hereinbefore described permits scaler 10 to be tuned to a particular working frequency such that external controls are not necessary to maintain the desired frequency once it is attained. That feature of the invention is particularly advantageous for it permits operation of the instrument without necessitating operator correction of frequency deviations which might be induced by variations in control elements.

Although this invention has been described with reference to a dental scler, it is also applicable to vibratory devices of like or similar configuration which are used for other purposes, such as medical, veterinary, and general industrial cleaning, polishing and deburring. Such vibratory devices can have water, air, paraffin, or other fluid materials transported through in accordance with the teachings of this invention.

The dental scaler or vibratory device of this invention can be utilized with the tips described in copending applications Ser. No. 4,283,174 issued Aug. 11, 1981 "Dental Scaler Having Scaling Tip Particularly Suitable For Circular or Ellipsoidal Patterns of Vibration," and Ser. No. 4,283,175 issued Aug. 11, 1981, entitled "Dental Scaler Having Scaling Tip With Rounded Edge Work Surfaces Particularly Suitable For Circular or Ellipsoidal Patterns of Vibration," filed concurrently herewith. If desired the dental scaler or vibratory device of this invention can be further modified in accordance with the teachings of any or all of copending applications Ser. Nos. 12,631, filed Feb. 16, 1979; Ser. No. 26,378, filed Apr. 2, 1979, now U.S. Pat. No. 4,260,380 and Ser. No. 91,012, entitled "Vibratory Device Having Tool Assembly With Fluid Transport Means," filed concurrently herewith. The above applications are incorporated herein by reference to the extent necessary to supplement or complete the disclosure hereof.

While this invention has been described with reference to specific embodiments thereof, it should be understood by those skilled in this art that various changes may be made and equivalents may be substituted without departing from the true spirit and scope of the invention. In addition, various novel elements, as described herein can be used individually or collectively, as desired. All such modifications are intended to be within the scope of the claims appended hereto.

What is claimed is:

1. In a dental scaler comprising elongated casing means having a proximal end and a distal end; resilient support means within said casing means; a substantially rigid hollow shaft supported within said elongated casing means by said resilient support means; work tool connecting means adjacent the distal end of said shaft, said work tool connecting means capable of operatively connecting a work tool to the distal end of said shaft, said shaft having fluid media inlet means and outlet means, respectively, for receiving and discharging fluid media, rotor means disposed about said shaft, said rotor means being positioned over said outlet means, said rotor means driveable about said shaft by the fluid media, said shaft and said rotor means each having a configuration and disposed with respect to each other so as to define a space therebetween for receiving said fluid media from said outlet means during movement of said rotor means about said shaft, the flow of the fluid media from said outlet means into the space driving said rotor means rotatively about said shaft so that said rotor means imparts vibratory movement to said shaft, the improvement comprising first means on said shaft for continuously correcting axial displacement of said rotor means from a centralized position over said outlet means when said rotor means is driven about said shaft.

2. The improvement of claim 1 wherein said first correction means comprises means on said shaft for biasing said rotor means against axial movement of said rotor means.

3. The improvement of claim 2 wherein said biasing means comprises a step on the outer surface of said shaft which is within the area of projection onto said shaft of said rotor means.

4. The improvement of claim 2 wherein said biasing means comprises a ramp on the outer surface of said shaft which commences within the area of projection onto said shaft of said rotor means and terminates outside of said area of projection.

5. The improvement of claim 1 wherein said first correction means comprises a cylindrical section of said shaft within the area of projection onto said shaft of said rotor means, said cylindrical section having a diameter greater than the diameter of those portions of said shaft adjacent said cylindrical section.

6. The improvement of claim 5 wherein said cylindrical section of said shaft is formed by a step at each end of said cylindrical section.

7. The improvement of claim 5 wherein said cylindrical section of said shaft is formed by an inclined surface at each end of said cylindrical section.

8. The improvement of claim 7 wherein the inclined surfaces are of equal length.

9. The improvement of claim 5 wherein the diameter of said cylindrical section is about 0.001–0.002 inch greater than the diameter of those portions of said shaft adjacent said cylindrical section.

10. The improvement of claim 5 wherein the length of said cylindrical section is less than the length of said rotor means.

11. The improvement of claim 10 wherein the ratio of the length of said cylindrical section to the length of said rotor means is between about 0.85–0.97.

12. The improvement of claim 1 further comprising second correction means associated with said rotor means.

13. The improvement of claim 12 wherein said second correction means comprises rotor walls having chamfered inside end edges.

14. The improvement of claim 13 wherein the chamfer is between about 30°–65°.

15. The improvement of claim 14 wherein the chamfer is between about 40°–50°.

16. The improvement of claim 13 wherein the surface roughness of the inner surface of said rotor means is smoother than about 20 micro-inches.

17. The improvement of claim 13 wherein said inside end edges of said rotor means are free from radially extending burrs.

18. The improvement of claim 1 wherein said outlet means comprises at least one passageway in the wall of said shaft within the area of projection of said rotor means onto said shaft, said passageway having a chamfer formed on its outermost edge.

19. The improvement of claim 18 wherein said passageway has an axis spaced from the longitudinal axis of said shaft.

20. The improvement of claim 18 wherein said outlet means comprises a plurality of passageways extending through the wall of said shaft, said passageways having a chamfer at their outermost edge.

21. The improvement of claim 20 wherein said plurality of passageways are arranged to direct substantially equal amounts of the fluid media through each end opening of the space defined by said rotor means and said shaft.

22. The improvement of claim 20 or 21 wherein the inner edges of said passageways are free from burrs.

23. The improvement of claim 18 further comprising second correction means associated with said rotor means.

24. The improvement of claim 23 wherein said second correction means comprises rotor walls having chamfered, inside end edges.

25. The improvement of claim 24 wherein the chamfer is between about 30°-65°.

26. The improvement of claim 25 wherein the chamfer is between about 40°-50°.

27. The improvement of claim 23 wherein the surface roughness of the inner surface of said rotor means is smoother than about 20 micro-inches.

28. The improvement of claim 27 wherein said inside end edges of said rotor are free from radially extending burrs.

29. A vibratory device comprising:
a sustantially rigid hollow shaft;
rotor means disposed about said shaft;
inlet and outlet means, respectively associated with said shaft for receiving and discharging fluid media, said rotor means positioned about said shaft and said outlet means, said shaft and said rotor means defining a space therebetween for receiving fluid media from said outlet means during movement of said rotor means about said shaft, the flow of the fluid media rotatively driving said rotor means about said shaft so that said rotor means imparts vibratory movement to said shaft;
means for supporting and operably connecting said shaft to an object to be vibrated; and
first means on said shaft for continuously correcting axial displacement of said rotor means from a centralized position over said outlet means when said rotor means is driven about said shaft.

30. The vibratory device of claim 29 wherein said correction means comprises a cylindrical section of said shaft within the area of projection onto said shaft of said rotor means, said cylindrical section having a diameter greater than the diameter of those portions of said shaft adjacent said cylindrical section.

31. The vibratory device of claim 30 wherein said cylindrical section is formed by a step at each end of said cylindrical section.

32. The vibratory device of claim 30 wherein said cylindrical section is formed by an inclined surface at each end of said cylindrical section.

33. The vibratory device of claim 32 wherein the inclined surfaces are of equal length.

34. The vibratory device of claim 30 wherein the diameter of said cylindrical section is about 0.001-0.002 inch greater than those portions of said shaft adjacent said cylindrical section.

35. The vibratory device of claim 30 wherein the length of said cylindrical section is less than the length of said rotor means.

36. The vibratory device of claim 35 wherein the ratio of the length of said cylindrical section to the length of said rotor means is between about 0.85-0.97.

37. The vibratory device of claim 29 further comprising second correction means associated with said rotor means.

38. The vibratory device of claim 37 wherein said second correction means comprises rotor walls having chamfered inside end edges.

39. The vibratory device of claim 38 wherein the chamfer is between about 30°-65°.

40. The vibratory device of claim 39 wherein the chamfer is between about 40°-50°.

41. The vibratory device of claim 38 wherein the surface roughness of the inner surface of said rotor means is smoother than about 20 micro-inches.

42. The vibratory device of claim 38 wherein said inside end edges are free from radially extending burrs.

43. A drive shaft for a vibratory device comprising a substantially rigid, hollow shaft having a distal end and a proximal end, a section of said shaft intermediate said distal and proximal ends having a diameter greater than the diameter of those portions of said shaft adjacent said section, said shaft having at least one passageway extending through the wall of said section of said shaft substantially centrally positioned with respect to the ends of said section, each of said ends of said section being joined to the adjacent shaft surface by a step.

44. A drive shaft for a vibratory device comprising a substantially, rigid, hollow shaft having a distal end and a proximal end, a section of said shaft intermediate said distal and proximal ends having a diameter greater than the diameter of those portions of said shaft adjacent said section, said shaft having at least one passageway extending through the wall of said section of said shaft substantially centrally positioned with respect to the ends of said section, each of said ends of said section being joined to the adjacent shaft surface by an inclined surface.

45. The drive shaft of claim 44 wherein said inclined surfaces are of equal length.

46. The drive shaft of claims 43, 44 or 45 wherein said section is substantially cylindrical having a diameter between about 0.001-0.002 inch greater than the diameter of those portions of said shaft adjacent said section.

47. The drive shaft of claim 46 wherein said section is adapted to lie entirely within the area of projection of a rotor means disposed about said shaft and said passageway(s).

48. A rotor for a vibratory device comprising a rigid, hollow cylinder having an inside wall with a surface roughness smoother than 20 micro-inches and inside end edges of said wall being chamfered.

49. The rotor of claim 48 wherein the chamfer is between about 30°-65°.

50. The rotor of claim 49 wherein the chamfer is between about 40°-50°.

51. A dental scaler comprising elongated casing means having a proximal end and a distal end, support means within said casing means including a first support means, a substantially rigid hollow shaft supported within said elongated casing means by said support means, said first support means being positioned near the distal end of said casing means, said first support means being positioned on said shaft at a node of the standing wave form developed in said shaft in a selected vibratory mode, said first support means being sufficiently non-resilient to bias said shaft in a selected vibratory mode, work tool connecting means adjacent the distal end of said shaft, said work tool connecting means capable of operatively connecting a work tool to the distal end of said shaft, said shaft having fluid media inlet means and outlet means, respectively, for receiving and discharging fluid media, rotor means disposed about said shaft, said rotor means being positioned over said outlet means, said rotor means driveable about said shaft by the fluid media, said shaft and said rotor means each having a configuration and disposed with respect to each other so as to define a space therebetween for receiving the fluid media from said outlet means during movement of said rotor means about said shaft, the flow of the fluid media from said outlet means into the space driving said rotor means rotatively about said shaft so that said rotor means imparts vibratory movement to said shaft.

52. The dental scaler of claims 51 wherein said support means includes second support means, said second support means being resilient and being located near the proximal end of said casing means.

53. The dental scaler of claim 51 further comprising water transport means within said casing means and water seal assembly means located within said shaft near the distal end thereof and in sealing engagement therewith, said first support means located substantially at the position of said water seal assembly means.

54. The dental scaler of claim 51 wherein said first support means is an O-ring surrounding said shaft.

55. The dental scaler of claim 54 wherein said O-ring is less than 70% resilient.

56. The dental scaler of claim 55 wherein said O-ring is about 60% resilient.

57. The dental scaler of claims 51, 52, 53, 54, 55 or 56 further comprising first means on said shaft for continuously correcting axial displacement of said rotor means from a centralized position over said outlet means when said rotor means is driven about said shaft.

58. The dental scaler of claim 57 wherein said first correction means comprises a cylindrical section of said shaft within the area of projection of said rotor means onto said shaft, said cylindrical section having a diameter greater than the diameter of those portions of said shaft adjacent said cylindrical section.

59. The dental scaler of claim 58 wherein said cylindrical section of said shaft is formed by a step at each end of said cylindrical section.

60. The dental scaler of claim 59 wherein the diameter of said cylindrical section is about 0.001–0.002 inch greater than the diameter of those portions of said shaft adjacent said cylindrical section.

61. The dental scaler of claim 60 wherein the length of said cylindrical section is less than the length of said rotor means.

62. The dental scaler of claim 61 wherein the ratio of the length of said cylindrical section to the length of said rotor means is between about 0.85–0.97.

63. The dental scaler of claim 57 further comprising second correction means associated with said rotor means.

64. The dental scaler of claim 63 wherein said second correction means comprises rotor walls having chamfered inside end edges.

65. The dental scaler of claim 64 wherein said inside end edges of said rotor means are free from radially extending burrs.

66. The dental scaler of claim 63 wherein said outlet means comprises at least one passageway in the wall of said shaft within the area of projection of said rotor means onto said shaft, said passageway having a chamfer formed on its outer most edge.

67. A vibratory device comprising:
a casing means;
support means including first support means within said casing means;
a substantially rigid hollow shaft supported by said support means within said casing means;
rotor means disposed about said shaft;
inlet and outlet means, respectively, associated with said shaft for receiving and discharging fluid media, said rotor means positioned about said shaft and said outlet means, said shaft and said rotor means defining a space therebetween for receiving fluid media from said outlet means during movement of said rotor means about said shaft, the flow of the fluid media rotatively driving said rotor means about said shaft so that said rotor means imparts vibratory movement to said shaft;
means for operably connecting said shaft to an object to be vibrated;
said support means including a first support means supporting said shaft at a position near the distal end of said casing means, said first support means being positioned on said shaft at a node of the standing wave form developed in said shaft in a selected vibratory mode, said first support means being sufficiently non-resilient to bias said scaler to operate in the selected vibratory mode.

68. The vibratory device of claim 67 wherein said support means includes second support means for said shaft near the proximal end thereof.

69. The vibratory device of claim 68 wherein said second support means is resilient and said first support means is less resilient than said second support means.

70. The vibratory device of claim 69 wherein said first support means is less than 70% resilient.

71. The vibratory device of claim 70 wherein said first support means is about 60% resilient.

72. The vibratory device of claims 70 or 71 wherein said first support means is an O-ring.

* * * * *